United States Patent [19]

Kirstgen et al.

[11] Patent Number: 5,506,254
[45] Date of Patent: Apr. 9, 1996

[54] PYRAZOYLY DERIVATIVES AND THEIR USE

[76] Inventors: Reinhard Kirstgen, Erkenbrechtstr.23e, 67434 Neustadt; Hartmann König, Blumenstr.16, 69115 Heidelberg; Hubert Sauter, Neckarpromenade 20, 68167 Mannheim; Volker Harries, Immengärtenweg 29e, 67227 Frankenthal; Gisela Lorenz, Erlenweg 13, 67434 Hambach; Eberhard Ammermann, Von-Gagern-Str.2, 64646 Heppenheim, all of Germany

[21] Appl. No.: 498,759
[22] Filed: Jul. 6, 1995

[30] Foreign Application Priority Data

Jul. 6, 1994 [DE] Germany ............... 44 23 615.8

[51] Int. Cl.⁶ ............... A01N 43/56; C07D 231/12
[52] U.S. Cl. ............... 514/406; 514/252; 514/341; 514/370; 514/380; 544/238; 544/322; 544/328; 544/331; 544/405; 546/279; 548/194; 548/245; 548/246; 548/360.5; 548/365.7; 548/366.1; 548/375.1; 548/377.1; 548/372.1
[58] Field of Search ............... 548/377.1; 514/406

[56] References Cited

U.S. PATENT DOCUMENTS

5,194,662  3/1993  Brand et al. ............... 560/35

FOREIGN PATENT DOCUMENTS

| 21005 | 2/1993 | Australia . |
|---|---|---|
| 2094359 | 4/1993 | Canada . |
| 398692 | 11/1990 | European Pat. Off. . |
| 468775 | 1/1992 | European Pat. Off. . |
| 477631 | 4/1992 | European Pat. Off. . |
| 5-255012 | 3/1992 | Japan . |
| 5-294948 | 4/1992 | Japan . |
| 2253624 | 9/1992 | United Kingdom . |
| 92/13830 | 8/1992 | WIPO . |
| 93/08180 | 4/1993 | WIPO . |
| 93/07116 | 4/1993 | WIPO . |
| 94/05626 | 3/1994 | WIPO . |
| 94/11334 | 5/1994 | WIPO . |

OTHER PUBLICATIONS

Kirstgen et al, *Chemical Abstracts*, vol. 121, No. 255,793 (1994).

*Primary Examiner*—R. W. Ramsuer

[57] ABSTRACT

Pyrazolyl derivatives of the general formula I

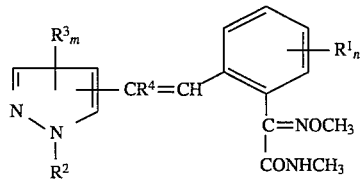

where the indices and the substituents have the following meanings:

n is is 0, 1, 2, 3 or 4, it being possible for the radicals $R^1$ to be different if n is greater than 1;

m is 0, 1 or 2, it being possible for the radicals $R^3$ to be different if m is greater than 1;

$R^1$ is nitro, cyano, halogen,
alkyl, haloalkyl, alkoxy, haloalkoxy or alkylthio,
unsubstituted or substituted phenyl or phenoxy;

$R^2$ is hydrogen,
unsubstituted or substituted alkyl, alkenyl or alkynyl,
an unsubstituted or substituted, saturated or mono- or diunsaturated ring,
an unsubstituted or substituted, mono- or binuclear aromatic radical;

$R^3$ is nitro, cyano, halogen, alkyl, haloalkyl, alkoxy or haloalkoxy;

$R^4$ is hydrogen, cyano, halogen, alkyl or haloalkyl, processes for their preparation and their use are described.

4 Claims, No Drawings

PYRAZOYLY DERIVATIVES AND THEIR USE

The present invention relates to pyrazolyl derivatives of the formula I

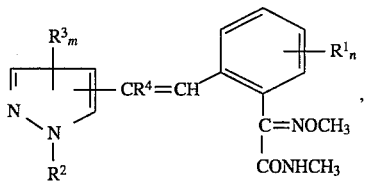

where the indices and the substituents have the following meanings:

n is 0, 1, 2, 3 or 4, it being possible for the substituents $R^1$ to be different if n is greater than 1;

m is 0, 1 or 2, it being possible for the radicals $R^3$ to be different if m is greater than 1;

$R^1$ is nitro, cyano, halogen, $C_1$–$C_4$-alkyl, $C_1$–$C_4$-haloalkyl, $C_1$$C_4$-alkoxy, $C_1$$C_4$-haloalkoxy, $C_1$–$C_4$-alkylthio, phenyl or phenoxy, where the aromatic radicals can carry one to five halogen atoms and/or one to three of the following radicals: nitro, cyano, $C_1$–$C_4$-alkyl, $C_1$–$C_4$-haloalkyl, $C_1$–$C_4$-alkoxy, $C_1$–$C_4$-haloalkoxy and $C_1$–$C_4$-alkylthio;

or in the case where n is greater than 1, a 1,3-butadiene-1,4-diyl group bonded to two adjacent C atoms of the phenyl radical, which in turn can carry one to our halogen atoms and/or one or two of the following radicals: nitro, cyano, $C_1$–$C_4$-alkyl, $C_1$–$C_4$-haloalkyl, $C_1$–$C_4$-alkoxy, $C_1$–$C_4$-haloalkoxy and $C_1$–$C_4$-alkylthio;

$R^2$ is hydrogen, unsubstituted or substituted alkyl, alkenyl or alkynyl, an unsubstituted or substituted, saturated or mono- or diunsaturated ring which, in addition to carbon atoms, can carry one of three of the following heteroatoms: oxygen, sulfur and nitrogen, or an unsubstituted or substituted, mono- or binuclear aromatic radical which, in addition to carbon atoms, can contain one to four nitrogen atoms and one oxygen or sulfur atom or one oxygen or sulfur atom as ring members;

$R^3$ is nitro, cyano, halogen, $C_1$–$C_4$-alkyl, $C_1$–$C_4$-haloalkyl, $C_1$–$C_4$-alkoxy or $C_1$–$C_4$-haloalkoxy;

$R^4$ is hydrogen, cyano, halogen, $C_1$–$C_4$-alkyl or $C_1$–$C_4$-haloalkyl.

The invention additionally relates to processes for preparing these compounds, compositions containing them and methods of controlling animal pests using these compositions.

2-Alkoxyiminoacetamides having fungicidal action are disclosed in the literature (EP-A 398 692, EP-A 468 775, WO-A 92/13,830, WO-A 93/07,116, WO-A 93/08,180, GB-A 2 253 624, JP-A 05/255,012, WO-A 94/05,626, JP-A 05/294,948). Derivatives of this type having insecticidal, acaricidal or nematocidal action are additionally described in EP-A 463 488, EP-A 477 631 and EP-A 567 828. The action of the known derivatives, however, is not always satisfactory.

The object of the present invention are compounds having an improved activity.

We have found that this object is achieved by the compounds defined at the outset. In addition, we have found processes for their preparation and their use in controlling pests.

The compounds I are prepared in a similar manner to various methods known per se from the literature. In the preparation, it is insignificant whether the (pyrazolyl)—$CR^4$=CH—(phenyl) group or the —C(=NOCH$_3$)—CONHCH$_3$ group is formed first. These groups are particularly preferably obtained by the processes described below, where for greater clarity the group not involved in the reaction in each case is represented in simplified form [(pyrazolyl)—$CR^4$=CH— ≡R*; —C(=NOCH$_3$)—CONHCH$_3$ ≡R#].

A: Process For The Synthesis Of The (Pyrazolyl)—$CR^4$=CH— Group

The (pyrazolyl)—$CR^4$=CH— group is obtained by reacting a suitable aldehyde either with a triphenylphosphonium compound in accordance with a Wittig reaction or with a phosphonate in accordance with a Wittig-Horner reaction.

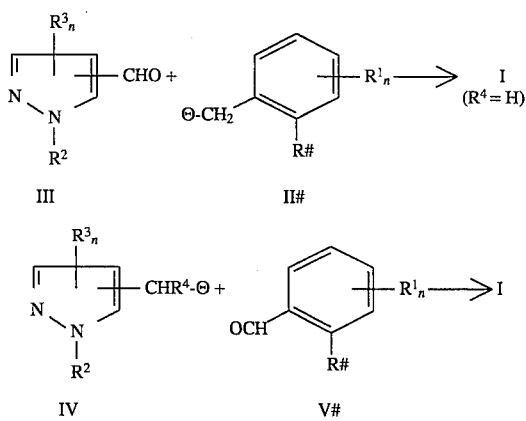

Θ in the formulae II and IV is $^{⊕}$P(C$_6$H$_5$)$_3$ $^{⊖}$Hal, where Hal is a halogen atom such as, in particular, chlorine, bromine or iodine, or PO(OR$^a$)$_2$, where R$^a$ is a C$_1$–C$_8$-alkyl group, in particular C$_1$–C$_4$-alkyl.

The reactions are customarily carried out at from 0° to 80° C., preferably from 20° to 60° C.

Suitable solvents are, for example, aromatic hydrocarbons (e.g. toluene, o-, m- and p-xylene), halogenated hydrocarbons (e.g. methylene chloride, chloroform, carbon tetrachloride and chlorobenzene), ethers (e.g. diethyl ether, diisopropyl ether, tert-butyl methyl ether, dioxane, anisole and tetrahydrofuran), nitriles (e.g. acetonitrile and propionitrile), alcohols (e.g. methanol, ethanol, propanol, isopropanol, butanol and tert-butanol), dimethyl sulfoxide, dimethylformamide, dimethylacetamide, 1,3-dimethylimidazolidin-2-one and 1,3-dimethyltetrahydro-2(1H)-pyrimidine, particularly preferably toluene, tetrahydrofuran, methanol and dimethylformamide. Mixtures of the solvents mentioned can also be used.

Suitable bases are generally inorganic compounds such as alkali metal and alkaline earth metal hydrides (e.g. lithium hydride, sodium hydride, potassium hydride and calcium hydride) and alkali metal amides (e.g. lithium amide, sodium amide and potassium amide) organometallic compounds such as alkali metal alkyls (e.g. methyllithium, butyllithium and phenyllithium), alkylmagnesium halides (e.g. methylmagnesium chloride) and also alkali metal and alkaline earth metal alkoxides (e.g. sodium methoxide, sodium ethoxide, potassium ethoxide, potassium tert-butoxide and dimethoxymagnesium), additionally organic bases such as tertiary amines (e.g. trimethylamine, triethylamine, diisopropylethylamine, N-methylpiperidine as well as bicyclic amines). Sodium hydride, sodium amide, sodium methoxide, potassium methoxide and potassium tert-butoxide are particularly preferred.

It may be advantageous for the reaction to add a catalytic amount of a crown ether (e.g. 18-crown-6 or 15-crown-5).

The bases are in general used in an equimolar amount, in an excess or if appropriate as a solvent.

The starting materials are customarily employed in equimolar amounts. It may be advantageous for completion of the reaction to employ one of the starting materials in an excess of from 1 mol % to 100 mol %, preferably from 1 mol % to 20 mol %, based on the second starting material.

The starting compounds II are prepared starting from the corresponding benzyl chlorides or bromides or iodides by reaction with triphenylphosphine or trialkyl phosphite according to methods known from the literature (cf. Houben-Weyl, Methoden der organischen Chemie (Methods of Organic Chemistry) Vol. 12/1, page 579 ff and page 433 ff, Verlag Thieme, Stuttgart 1963).

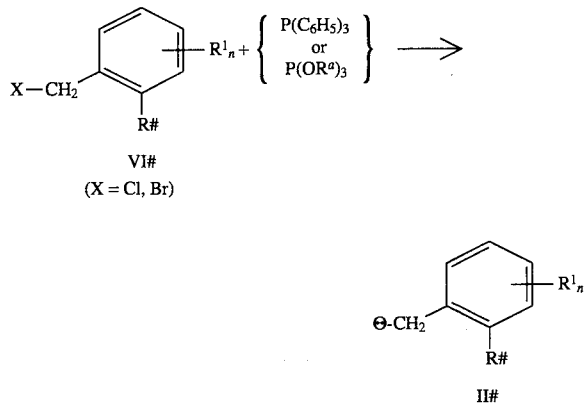

VI#
(X = Cl, Br)

II#

The preparation of the benzyl compounds is described in EP-A 477 631.

The pyrazole derivatives III and IV are known from the literature or can be prepared by the processes described there [cf. *J. Heterocycl. Chem.* 24 (1987), 739; J. Heterocycl. Chem. 25 (1988), 555; *J. Heterocycl. Chem.* 2a (1991), 1545; Bull. Chem. Soc. Jpn. 58 (1985), 1841; *Bull. Chem. Soc. Jpn.* 59 (1986), 2631; *Chem. Lett.* 1982, 543; J. Chem. Soc. 1957, 3314; Liebigs Ann. Chem. 1985, 1377; Synthesis, 1983, 566].

The functional group (aldehyde or methylene phosphorus compound) needed in each case can be obtained by formylation [cf. Pharmazie 30 (1975), 157], reduction and oxidation [cf. Heterocycles 23 (1985), 1417; J. Her. Chem. 27 (1990), 1933], halogenation [cf. J. Het. Chem. 14 (1977), 1171], and reaction with triphenylphosphine or trialkyl phosphite.

Compounds IV where $R^4$ is halogen can be obtained analogously to the method described in EP-A 544 587.

B: Process For The Synthesis Of The —C(=NOCH$_3$)—CONHCH$_3$ Group

The compounds I are obtained by aminolysis of the corresponding 2-methoxyiminophenylacetic acid esters II (cf. Houben-Weyl Vol. E5, page 983 ff).

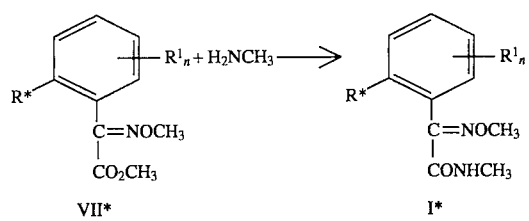

VII*  I*

The reaction is customarily carried out at from 0° to 60° C., preferably from 10° to 30° C.

Methylamine can either be introduced as a gas or metered into a solution of the compounds VII as an aqueous solution.

Suitable solvents are aromatic hydrocarbons (e.g. toluene, o-, m- and p-xylene), halogenated hydrocarbons (e.g. methylene chloride, chloroform, carbon tetrachloride and chlorobenzene), ethers (e.g. diethyl ether, diisopropyl ether, tert-butyl methyl ether, dioxane, anisole and tetrahydrofuran) and alcohols (e.g. methanol, ethanol, propanol, isopropanol, butanol and tert-butanol), particularly preferably methanol, toluene and tetrahydrofuran. Mixtures of the solvents mentioned can also be used.

Other processes for the preparation of this group are disclosed in the literature cited at the outset.

Conversion to the —C(=NOCH$_3$)—CONHCH$_3$ group can be carried out on an of the intermediates or precorsors marked by #.

On account of their C=C and C=N double bonds, the compounds I can be obtained during preparation as E/Z isomer mixtures which can be separated into the individual compounds in a customary manner, e.g. by crystallization or chromatography.

If isomer mixtures are obtained in the synthesis, in general separation is not necessary, as the individual isomers can be converted to one another during preparation for application or on application (e.g. by the action of light, acid or base). Corresponding conversions can also take place after application, for example in the treated plant during the treatment of plants or in the pest to be controlled.

With reference to the C=N double bond, the E isomers of the compounds are preferred with respect to their activity (configuration based on the OCH$_3$ group in relation to the CONHCH$_3$ group).

With reference to the $CR^4$=CH double bond, the E isomers are preferred with respect to their activity (configuration based on the pyrazole radical in relation to the phenyl ring).

In the definitions of the compounds I given at the outset collective terms were used which are generally representative of the following groups:

halogen: fluorine, chlorine, bromine and iodine;

alkyl: saturated, straight-chain or branched hydrocarbon radicals having 1 to 4 or 10 carbon atoms, e.g. $C_1$–$C_6$-alkyl such as methyl, ethyl, propyl, 1-methylethyl, butyl, 1-methylpropyl, 2-methylpropyl, 1,1-methylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl;

haloalkyl: straight-chain or branched alkyl groups having 1 to 4 carbon atoms (as mentioned above), it being possible for the hydrogen atoms in these groups to be partly or completely replaced by halogen atoms such as mentioned above, e.g. $C_1$–$C_2$-halo alkyl such as chloromethyl, dichloromethyl, trichloromethyl, fluoromethyl, difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl and pentafluoroethyl;

alkoxy: straight-chain or branched alkyl groups having 1 to 4 carbon atoms (as mentioned above), which are bonded to the structure via an oxygen atom (—O—);

haloalkoxy: straight-chain or branched haloalkyl groups having 1 to 4 carbon atoms (as mentioned above), which are bonded to the structure via an oxygen atom (—O—);

alkylthio: straight-chain or branched alkyl groups having 1 to 4 carbon atoms (as mentioned above), which are bonded to the structure via a sulfur atom (—S—);

alkenyl: unsaturated, straight-chain or branched hydrocarbon radicals having 2 to 10 carbon atoms and a double bond in any desired position, e.g. $C_2$–$C_6$-alkenyl such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl;

alkynyl: straight-chain or branched hydrocarbon groups having 2 to 10 carbon atoms and a triple bond in any desired position, e.g. $C_2$–$C_6$-alkynyl such as ethynyl, 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 1-ethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl and 1-ethyl-1-methyl-2-propynyl;

unsubstituted or substituted, saturated or mono- or diunsaturated ring which, in addition to carbon atoms, can carry one to three of the following heteroatoms: oxygen, sulfur and nitrogen: 3- to 6-membered carbo- or heterocycles, such as $C_3$–$C_6$-cycloalkyl, e.g. cyclopropyl, cyclopentyl and cyclohexyl;

$C_5$–$C_6$-cycloalkenyl, e.g. cyclopentenyl and cyclohexenyl;

heterocyclyl, e.g. tetrahydrofuranyl, tetrahydrothienyl, pyrrolidinyl, isoxazolidinyl, isothiazolidinyl, pyrazolidinyl, oxazolidinyl, thiazolidinyl, imidazolidinyl, oxadiazolidinyl, thiadiazolidinyl, triazolidinyl, dihydrofuryl, dihydrothienyl, pyrrolinyl, isoxazolinyl, isothiazolinyl, dihydropyrazolyl, dihydrooxazolyl, piperidinyl, dioxanyl, morpholinyl, tetrahydropyranyl, tetrahydrothiopyranyl, tetrahydropyridazinyl, tetrahydropyrimidinyl, tetrahydropyrazinyl and tetrahydrotriazinyl, preferably tetrahydrofuranyl, tetrahydrothienyl, pyrrolidinyl, isoxazolidinyl, isothiazolidinyl, oxazolidinyl, dihydrothienyl, isoxazolinyl, piperidinyl, dioxanyl and tetrahydropyranyl;

an unsubstituted or substituted, mono- or binuclear aromatic radical which, in addition to carbon atoms, can contain one to four nitrogen atoms and one oxygen or sulfur atom or one oxygen or sulfur atom as ring members (hetaryl):

5-membered heteroaryl: 5-membered ring heteroaryl groups which, in addition to carbon atoms, can contain one to four nitrogen atoms or one to three nitrogen atoms and/or one sulfur or oxygen atom as ring members, e.g. 2-furyl, 3-furyl, 2-thienyl, 3-thienyl, 2-pyrrolyl, 3-pyrrolyl, 3-isoxazotyl, 4-isoxazolyl, 5-isoxazolyl, 3-isothiazolyl, 4-isothiazolyl, 5-isothiazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 4-imidazolyl, 1,2,4-oxadiazol-3-yl, 1,2,4-oxadiazol-5-yl, 1,2,4-thiadiazol-3-yl, 1,2,4-thiadiazol-5-yl, 1,2,4-triazol-3-yl, 1,3,4-oxadiazol-2-yl, 1,3,4-thiadiazol-2-yl and 1,3,4-triazol-2-yl;

benzo-fused 5-membered heteroaryl, containing one to three nitrogen atoms or one nitrogen atom and one oxygen or sulfur atom: 5-membered ring heteroaryl groups which in addition to carbon atoms can contain one to four nitrogen atoms or one to three nitrogen atoms and one sulfur or oxygen atom as ring members, and in which two adjacent carbon ring members or one nitrogen and one adjacent carbon ring member can be bridged by a buta-1,3-diene-1,4-diyl group;

5-membered heteroaryl bonded via nitrogen, containing one to four nitrogen atoms, or benzo-fused 5-membered heteroaryl bonded via nitrogen, containing one to three nitrogen atoms: 5-membered ring heteroaryl groups which in addition to carbon atoms can contain one to four nitrogen atoms or one to three nitrogen atoms as ring members, and in which two adjacent carbon ring members or one nitrogen and one adjacent carbon ring member can be bridged by a buta-1,3-diene-1,4-diyl group, where these rings are bonded to the structure via one of the nitrogen ring members;

6-membered heteroaryl, containing one to three or one to four nitrogen atoms: 6-membered ring heteroaryl groups which in addition to carbon atoms can contain one to three or one to four nitrogen atoms as ring members, e.g. 2-pyridinyl, 3-pyridinyl, 4-pyridinyl, 3-pyridazinyl, 4-pyridazinyl, 2-pyrimidinyl, 4-pyrimidinyl, 5-pyrimidinyl, 2-pyrazinyl, 1,3,5-triazin-2-yl and 1,2,4-triazin-3-yl.

The addition of "unsubstituted or substituted" with respect to the alkyl, alkenyl and alkynyl radicals is intended to express that these groups can be partly or completely halogenated and/or can carry one of the following radicals:

nitro, cyano, thiocyanato,

- $C_1$–$C_6$-alkylcarbonyl [alkyl groups having 1 to 6 carbon atoms (as mentioned above), which are bonded to the structure via a carbonyl group (—CO—)], $C_1$–$C_6$-alkylcarbonyloxy [alkyl groups having 1 to 6 carbon atoms (as mentioned above), which are bonded to the structure via a carbonyloxy group (—$CO_2$—)], $C_1$–$C_6$-alkylcarbonylamino [alkyl groups having 1 to 6 carbon atoms (as mentioned above), which are bonded to the structure via a carbonylamino group (—CONH—)],
- $C_1$–$C_6$-alkoxy, $C_1$–$C_6$-alkoxycarbonyl [alkoxy groups having 1 to 6 carbon atoms (as mentioned above), which are bonded to the structure via a carbonyl group (—CO—)], $C_1$–$C_4$-haloalkoxy,
- $C_1$–$C_4$-alkylthio, $C_1$–$C_6$-alkylthiocarbonyl [alkylthio groups having 1 to 6 carbon atoms (as mentioned above), which are bonded to the structure via a carbonyl group (—CO—)],
- $C_1$–$C_6$-alkylamino [alkyl groups having 1 to 6 carbon atoms (as mentioned above), which are bonded to the structure via an amino group (—NH—)], $C_1$–$C_6$-alkylaminocarbonyl [alkyl groups having 1 to 6 carbon atoms (as mentioned above), which are bonded to the structure via an aminocarbonyl group (—NHCO—)], di-$C_1$–$C_6$-alkylamino [two alkyl groups having 1 to 6 carbon atoms, which are independent of one another and are bonded to the structure via a nitrogen atom (:N—)], di-$C_1$14 $C_6$-alkylaminocarbonyl [dialkylamino groups (as mentioned above), which are bonded to the structure via a carbonyl group],
- $C_3$–$C_6$-alkenyloxy [alkenyl groups having three to six carbon atoms and a double bond which is not in the 1-position, which are bonded to the structure via an oxygen atom (—O—)],
- $C_3$–$C_6$-alkynyl [alkynyl groups having three to six carbon atoms and a triple bond which is not in the 1-position, which are bonded to the structure via an oxygen atom (—O—)],
- $C_3$–$C_7$-cycloalkyl, $C_3$–$C_7$-cycloalkoxy, $C_3$–$C_7$-cycloalkylthio, $C_3$–$C_7$-cycloalkylamino [alicyclic radicals having 3 to 7 carbon atoms bonded directly or via an oxygen-, sulfur- or NH—, e.g. cyclopropyl, cyclobutyl and cyclohexyl, in particular cyclopropyl or the corresponding oxy, thio and amino groups], $C_5$–$C_7$-cycloalkenyl, $C_5$–$C_7$-cycloalkenyloxy, $C_5$–$C_7$-cycloalkenylthio, $C_5$–$C_7$-cycloalkenylamino, [alicyclic radicals having 5 to 7 carbon atoms and a double bond in the ring, bonded directly or via an oxygen-, sulfur- or NH—, e.g. cyclopentenyl and cyclohexenyl, in particular cyclopentenyl or the corresponding oxy, thio and amino groups],
- phenyl, phenoxy, phenylthio and phenylamino, where the phenyl rings in turn can be partly or completely halogenated and/or can carry one to three of the following radicals: cyano, nitro, $C_1$–$C_4$-alkyl, $C_1$–$C_4$-haloalkyl, $C_1$–$C_4$-alkoxy, $C_1$–$C_4$-haloalkoxy and $C_1$–$C_4$-alkylthio;
- 5- or 6-membered heteroaryl, heteroaryloxy, heteroarylthio or heteroarylamino (as mentioned above, in particular 3-furyl, 2-thienyl, 3-thienyl, 3-isoxazolyl, 5-isoxazolyl, 4-oxazolyl, 1,3,4-thiadiazolyl, 3-pyridinyl and 5-pyrimidinyl), where these ring systems can be partly or completely halogenated and/or can carry one or two of the following groups: cyano, nitro, $C_1$–$C_4$-alkyl, $C_1$–$C_4$-haloalkyl, $C_1$–$C_4$-alkoxy, $C_1$–$C_4$-haloalkoxy and $C_1$–$C_4$-alkylthio.

The addition of "unsubstituted or substituted" with respect to the cyclic (aliphatic or aromatic) radicals is intended to express that these groups can be partly or completely halogenated and/or can carry one to three of the following radicals:

nitro, cyano, thiocyanato,

- $C_1$–$C_6$-alkyl, $C_1$–$C_6$-alkylcarbonyl [alkyl groups having 1 to 6 carbon atoms (as mentioned above), which are bonded to the structure via a carbonyl group (—CO—)], $C_1$–$C_6$-alkylcarbonyloxy [alkyl groups having 1 to 6 carbon atoms (as mentioned above), which are bonded to the structure via a carbonyloxy group (—$CO_2$—)], $C_1$–$C_6$-alkylcarbonylamino [alkyl groups having 1 to 6 carbon atoms (as mentioned above), which are bonded to the structure via a carbonylamino group (—CONH—)], $C_1$–$C_4$-haloalkyl,
- $C_1$–$C_6$-alkoxy, $C_1$–$C_6$-alkoxycarbonyl [alkoxy groups having 1 to 6 carbon atoms (as mentioned above), which are bonded to the structure via a carbonyl group (—CO—)], $C_1$–$C_4$-haloalkoxy,
- $C_1$–$C_4$-alkylthio, $C_1$–$C_6$-alkylthiocarbonyl [alkylthio groups having 1 to 6 carbon atoms (as mentioned above), which are bonded to the structure via a carbonyl group (—CO—)],
- $C_1$–$C_6$-alkylamino [alkyl groups having 1 to 6 carbon atoms (as mentioned above), which are bonded to the structure via an amino group (—NH—)], $C_1$–$C_6$-alkylaminocarbonyl [alkyl groups having 1 to 6 carbon atoms (as mentioned above), which are bonded to the structure via an aminocarbonyl group (—NHCO—)], di-$C_1$–$C_6$-alkylamino [two alkyl groups having 1 to 6 carbon atoms, which are independent of one another and are bonded to the structure via a nitrogen atom (:N—)], di-$C_1$–$C_6$-alkylaminocarbonyl [dialkylamino groups (as mentioned above), which are bonded to the structure via a carbonyl group],
- $C_2$–$C_6$-alkenyl, $C_3$–$C_6$-alkenyloxy [alkenyl groups having three to six carbon atoms and one double bond which is not in the 1-position, which are bonded to the structure via an oxygen atom (—O—)],
- $C_2$–$C_6$-alkynyl, $C_3$–$C_6$-alkynyloxy [alkynyl groups having three to six carbon atoms and a triple bond which is not in the 1-position, which are bonded to the structure via an oxygen atom (—O—)],
- $C_3$–$C_7$-cycloalkyl, $C_3$–$C_7$-cycloalkoxy, $C_3$–$C_7$-cycloalkylthio, $C_3$–$C_7$-cycloalkylamino [alicyclic radicals having 3 to 7 carbon atoms bonded directly or via an oxygen-, sulfur- or NH—, e.g. cyclopropyl, cyclobutyl and cyclohexyl, in particular cyclopropyl or the corresponding oxy-, thio- and amino groups], $C_5$–$C_7$-cycloalkenyl, $C_5$–$C_7$-cycloalkenyloxy, $C_5$–$C_7$-cycloalkenylthio, $C_5$–$C_7$-cycloalkenylamino, [alicyclic radicals having 5 to 7 carbon atoms and a double bond in the ring, bonded directly or via an oxygen-, sulfur- or NH—, e.g. cyclopentenyl and cyclohexenyl, in particular cyclopentenyl or the corresponding oxy, thio and amino groups], phenyl, phenoxy, phenylthio and phenylamino, where the phenyl rings in turn can be partly or completely halogenated and/or can carry one to three of the following radicals: cyano, nitro, $C_1$–$C_4$-alkyl, $C_1$–$C_4$-haloalkyl, $C_1$–$C_4$-alkoxy, $C_1$–$C_4$-haloalkoxy and $C_1$–$C_4$-alkylthio;

5- or 6-membered heteroaryl, heteroaryloxy, heteroarylthio or heteroarylamino (as mentioned above, in particular 3-furyl, 2-thienyl, 3-thienyl, 3-isoxazolyl, 5-isoxazolyl, 4-oxazolyl, 1,3,4-thiadiazolyl, 3-pyridinyl and 5-pyrimidinyl), where these ring systems can be partly or completely halogenated and/or can carry one or two of the following groups: cyano, nitro, $C_1$–$C_4$-alkyl, $C_1$–$C_4$-haloalkyl, $C_1$–$C_4$-alkoxy, $C_1$–$C_4$-haloalkoxy and $C_1$–$C_4$-alkylthio.

The statement "partly or completely halogenated" is intended to express that in groups characterized in this way the hydrogen atoms can be partly or completely replaced by identical or different halogen atoms as mentioned above.

With respect to their biological action, compounds I are preferred where n is 0 or 1.

Equally, compounds of the formula I are preferred where m is 0 or 1.

In addition, compounds I are preferred where $R^1$ is halogen, $C_1$–$C_4$-alkyl, $C_1$–$C_2$-haloalkyl, $C_1$–$C_4$-alkoxy, $C_1$–$C_2$-haloalkoxy, $C_1$–$C_2$-alkylthio or phenyl.

Additionally, compounds I are preferred where $R^2$ is unsubstituted or substituted aryl or heteroaryl.

Particularly preferred compounds I are those where $R^2$ is unsubstituted or substituted phenyl. Suitable substituents of the phenyl radical are in particular the following groups: halogen, cyano, $C_1$–$C_4$-alkyl, $C_1$–$C_2$-haloalkyl, $C_1$–$C_4$-alkoxy, $C_1$–$C_2$-haloalkoxy, phenyl or oxy-$C_1$–$C_2$-alkylideneoxy.

In addition, compounds I are particularly preferred where $R^2$ is unsubstituted or substituted 5-membered heteroaryl. In particular, compounds I are preferred where $R^2$ is unsubstituted or substituted thiazolyl, isoxazolyl or oxazolyl.

Suitable substituents of the 5-membered heteroaromatics are in particular the following groups: cyano, halogen, $C_1$–$C_6$-alkyl, $C_1$–$C_4$-haloalkyl, $C_1$–$C_6$-alkoxy, $C_1$–$C_4$-haloalkoxy and phenyl.

In addition, compounds I are particularly preferred where $R^2$ is unsubstituted or substituted 6-membered heteroaryl. In particular, compounds I are preferred where $R^2$ is unsubstituted or substituted pyridyl, pyrimidyl, pyridazinyl or pyrazinyl.

Suitable substituents of the 6-membered heteroaromatics are in particular the following groups: cyano, halogen, $C_1$–$C_6$-alkyl, $C_1$–$C_4$-haloalkyl, $C_1$–$C_6$-alkoxy, $C_1$–$C_4$-haloalkoxy and phenyl.

In addition, compounds I are preferred where $R^3$ is cyano, halogen, $C_1$–$C_2$-alkyl, $C_1$–$C_2$-haloalkyl, $C_1$–$C_2$-alkoxy or $C_1$–$C_2$-haloalkoxy.

In particular, compounds I are preferred where $R^3$ is chlorine, methyl or trifluoromethyl.

Equally, compounds I are preferred where $R^4$ is hydrogen or halogen.

Compounds I are particularly preferred where $R^4$ is hydrogen, fluorine or chlorine.

Of particular importance are also compounds I where the (pyrazolyl)—$CR^4$=CH— group is one of the following groups W.1 to W.23:

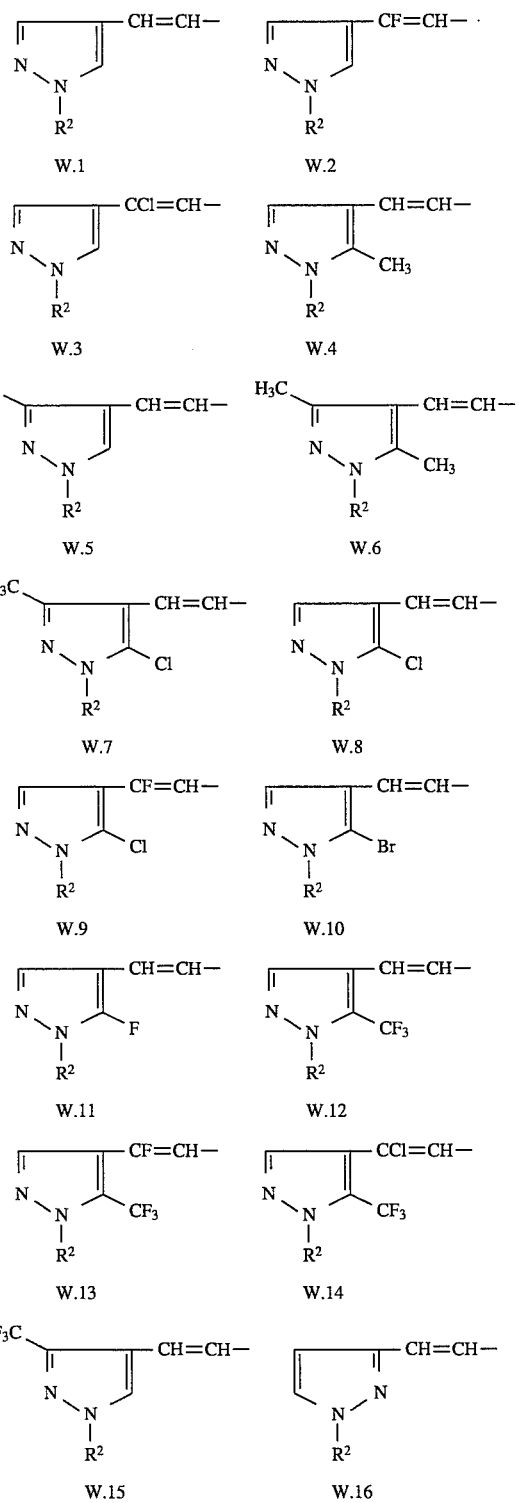

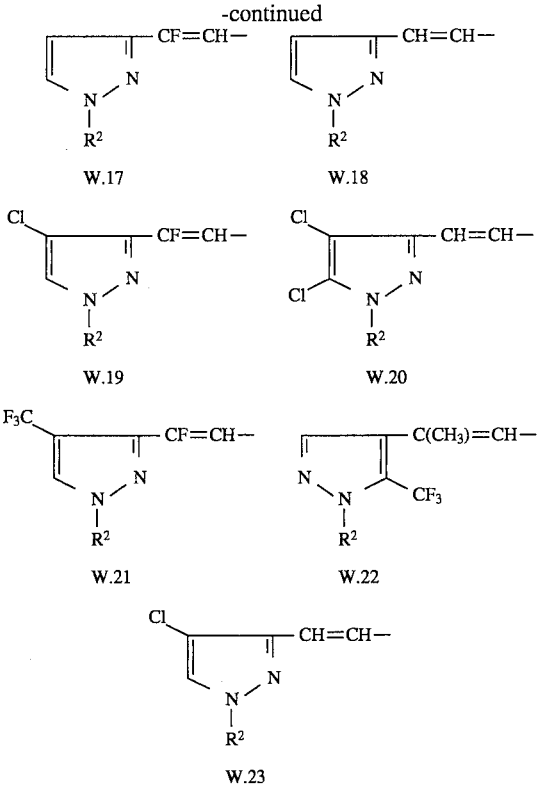

W.17, W.18, W.19, W.20, W.21, W.22, W.23

With respect to their use, the compounds I compiled in the following Tables are particularly preferred.

TABLE 1

Compounds of the formula I where the (pyrazolyl)—$CR^4$=CH— radical is the group W.1 and the combination of the substituents $R^1_n$ and $R^2$ for one compound in each case corresponds to one line of Table A

TABLE 2

Compounds of the formula I where the (pyrazolyl)—$CR^4$=CH— radical is the group W.16 and the combination of the substituents $R^1_n$ and $R^2$ for one compound in each case corresponds to one line of Table A.

TABLE 3

Compounds of the formula I where the (pyrazolyl)—$CR^4$=CH— radical is the group W.4 and the combination of the substituents $R^1_n$ and $R^2$ for one compound in each case corresponds to one line of Table A.

TABLE 4

Compounds of the formula I where the (pyrazolyl)—$CR^4$=CH— radical is the group W.8 and the combination of the substituents $R^1_n$ and $R^2$ for one compound an each case corresponds to one line of Table A.

TABLE 5

Compounds of the formula I where the (pyrazolyl)—$CR^4$=CH— radical is the group W.10 and the combination of the substituents $R^1_n$ and $R^2$ for one compound an each case corresponds to one line of Table A.

TABLE 6

Compounds of the formula I where the (pyrazolyl)—$CR^4$=CH— radical is the group W.12 and the combination of the substituents $R^1_n$ and $R^2$ for one compound an each case corresponds to one line of Table A.

TABLE 7

Compounds of the formula I where the (pyrazolyl)—$CR^4$=CH— radical is the group W.15 and the combination of the substituents $R^1_n$ and $R^2$ for one compound an each case corresponds to one line of Table A.

TABLE 8

Compounds of the formula I where the (pyrazolyl)—$CR^4$=CH— radical is the group W.2 and the combination of the substituents $R^1_n$ and $R^2$ for one compound an each case corresponds to one line of Table A.

TABLE 9

Compounds of the formula I where the (pyrazolyl)—$CR^4$=CH— radical is the group W.13 and the combination of the substituents $R^1_n$ and $R^2$ for one compound an each case corresponds to one line of Table A.

TABLE 10

Compounds of the formula I where the (pyrazolyl)—$CR^4$=CH— radical is the group W.23 and the combination of the substituents $R^1_n$ and $R^2$ for one compound an each case corresponds to one line of Table A.

TABLE A

| $R^1_n$ | $R^2$ |
|---|---|
| H | $C_6H_5$ |
| 3-Cl | $C_6H_5$ |
| 4-Cl | $C_6H_5$ |
| 6-Cl | $C_6H_5$ |
| 4-F | $C_6H_5$ |
| 4-OCH$_3$ | $C_6H_5$ |
| 3-CH$_3$ | $C_6H_5$ |
| 6-CH$_3$ | $C_6H_5$ |
| H | 2-F—$C_6H_4$ |
| H | 3-F—$C_6H_4$ |
| H | 4-F—$C_6H_4$ |
| H | 2,3-F$_2$—$C_6H_3$ |
| H | 2,4-F$_2$—$C_6H_3$ |
| H | 2,5-F$_2$—$C_6H_3$ |
| H | 2,6-F$_2$—$C_6H_3$ |
| H | 3,4-F$_2$—$C_6H_3$ |
| H | 3,5-F$_2$—$C_6H_3$ |
| H | 2-Cl—$C_6H_4$ |
| H | 3-Cl—$C_6H_4$ |
| 3-Cl | 3-Cl—$C_6H_4$ |
| 4-Cl | 3-Cl—$C_6H_4$ |
| 6-Cl | 3-Cl—$C_6H_4$ |
| 4-F | 3-Cl—$C_6H_4$ |
| 4-OCH$_3$ | 3-Cl—$C_6H_4$ |
| 3-CH$_3$ | 3-Cl—$C_6H_4$ |
| 6-CH$_3$ | 3-Cl—$C_6H_4$ |
| H | 4-Cl—$C_6H_4$ |
| 3-Cl | 4-Cl—$C_6H_4$ |
| 4-Cl | 4-Cl—$C_6H_4$ |
| 6-Cl | 4-Cl—$C_6H_4$ |
| 4-F | 4-Cl—$C_6H_4$ |
| 4-OCH$_3$ | 4-Cl—$C_6H_4$ |
| 3-CH$_3$ | 4-Cl—$C_6H_4$ |
| 6-CH$_3$ | 4-Cl—$C_6H_4$ |
| H | 2,3-Cl$_2$—$C_6H_3$ |
| H | 2,4-Cl$_2$—$C_6H_3$ |
| 3-Cl | 2,4-Cl$_2$—$C_6H_3$ |
| 4-Cl | 2,4-Cl$_2$—$C_6H_3$ |

TABLE A-continued

| $R^1n$ | $R^2$ |
|---|---|
| 6-Cl | 2,4-Cl$_2$—C$_6$H$_3$ |
| 4-F | 2,4-Cl$_2$—C$_6$H$_3$ |
| 4-OCH$_3$ | 2,4-Cl$_2$—C$_6$H$_3$ |
| 3-CH$_3$ | 2,4-Cl$_2$—C$_6$H$_3$ |
| 6-CH$_3$ | 2,4-Cl$_2$—C$_6$H$_3$ |
| H | 2,5-Cl$_2$—C$_6$H$_3$ |
| H | 2,6-Cl$_2$—C$_6$H$_3$ |
| H | 3,4-Cl$_2$—C$_6$H$_3$ |
| H | 3,5-Cl$_2$—C$_6$H$_3$ |
| H | 2,3,4-Cl$_3$—C$_6$H$_2$ |
| H | 2,3,5-Cl$_3$—C$_6$H$_2$ |
| H | 2,3,6-Cl$_3$—C$_6$H$_2$ |
| H | 2,4,5-Cl$_3$—C$_6$H$_2$ |
| H | 2,4,6-Cl$_3$—C$_6$H$_2$ |
| H | 3,4,5-Cl$_3$—C$_6$H$_2$ |
| H | 2-Br—C$_6$H$_4$ |
| H | 3-Br—C$_6$H$_4$ |
| H | 4-Br—C$_6$H$_4$ |
| H | 2,4-Br$_2$—C$_6$H$_3$ |
| H | 2-Br, 4-F—C$_6$H$_3$ |
| H | 2-Br, 4-Cl—C$_6$H$_3$ |
| H | 2-F, 4-Cl—C$_6$H$_3$ |
| H | 3-F, 4-Cl—C$_6$H$_3$ |
| H | 5-F, 3-Cl—C$_6$H$_3$ |
| H | 4-F, 2-Cl—C$_6$H$_3$ |
| H | 2-CN—C$_6$H$_4$ |
| H | 3-CN—C$_6$H$_4$ |
| H | 4-CN—C$_6$H$_4$ |
| H | 3-CN, 4-Cl—C$_6$H$_3$ |
| H | 4-NO$_2$—C$_6$H$_4$ |
| H | 4-H$_2$NC(=S)—C$_6$H$_4$ |
| H | 2-CH$_3$—C$_6$H$_4$ |
| H | 3-CH$_3$—C$_6$H$_4$ |
| H | 4-CH$_3$—C$_6$H$_4$ |
| H | 2,3-(CH$_3$)$_2$—C$_6$H$_3$ |
| H | 2,4-(CH$_3$)$_2$—C$_6$H$_3$ |
| H | 2,5-(CH$_3$)$_2$—C$_6$H$_3$ |
| H | 2,6-(CH$_3$)$_2$—C$_6$H$_3$ |
| H | 3,4-(CH$_3$)$_2$—C$_6$H$_3$ |
| H | 3,5-(CH$_3$)$_2$—C$_6$H$_3$ |
| H | 2,4,6-(CH$_3$)$_3$—C$_6$H$_2$ |
| H | 3,4,5-(CH$_3$)$_3$—C$_6$H$_2$ |
| H | 2-CH$_3$, 4-Cl—C$_6$H$_3$ |
| H | 3-CH$_3$, 4-Cl—C$_6$H$_3$ |
| H | 4-CH$_3$, 2-Cl—C$_6$H$_3$ |
| H | 5-CH$_3$, 3-Cl—C$_6$H$_3$ |
| H | 4-CH$_3$, 2-CN—C$_6$H$_3$ |
| H | 2-CH$_3$, 4-CN—C$_6$H$_3$ |
| H | 4-C$_2$H$_5$—C$_6$H$_4$ |
| H | 4-C(CH$_3$)$_3$—C$_6$H$_4$ |
| H | 3-C$_6$H$_5$—C$_6$H$_4$ |
| H | 4-C$_6$H$_5$—C$_6$H$_4$ |
| H | 2-CF$_3$—C$_6$H$_4$ |
| H | 3-CF$_3$—C$_6$H$_4$ |
| H | 4-CF$_3$—C$_6$H$_4$ |
| H | 3,5-(CF$_3$)$_2$—C$_6$H$_3$ |
| H | 2-Cl, 4-CF$_3$—C$_6$H$_3$ |
| H | 2-OCH$_3$—C$_6$H$_4$ |
| H | 3-OCH$_3$—C$_6$H$_4$ |
| H | 4-OCH$_3$—C$_6$H$_4$ |
| H | 2,4-(OCH$_3$)$_2$—C$_6$H$_3$ |
| H | 3,4-(OCH$_3$)$_2$—C$_6$H$_3$ |
| H | 2,5-(OCH$_3$)$_2$—C$_6$H$_3$ |
| H | 3,5-(OCH$_3$)$_2$—C$_6$H$_3$ |
| H | 2,6-(OCH$_3$)$_2$—C$_6$H$_3$ |
| H | 3,4,5-(OCH$_3$)$_3$—C$_6$H$_2$ |
| H | 2-CH$_3$, 4-OCH$_3$—C$_6$H$_3$ |
| H | 2-Cl, 4-OCH$_3$—C$_6$H$_3$ |
| H | 2-OC$_2$H$_5$—C$_6$H$_4$ |
| H | 3-OC$_2$H$_5$—C$_6$H$_4$ |
| H | 4-OC$_2$H$_5$—C$_6$H$_4$ |
| H | 2-OC(CH$_3$)$_3$—C$_6$H$_4$ |
| H | 3-OC(CH$_3$)$_3$—C$_6$H$_4$ |
| H | 4-OC(CH$_3$)$_3$—C$_6$H$_4$ |
| H | 2-OCF$_3$—C$_6$H$_4$ |
| H | 3-OCF$_3$—C$_6$H$_4$ |
| H | 4-OCF$_3$—C$_6$H$_4$ |
| H | 2-OCHF$_2$—C$_6$H$_4$ |
| H | 3-OCHF$_2$—C$_6$H$_4$ |
| H | 4-OCHF$_2$—C$_6$H$_4$ |
| H | 4-OCF$_2$CHF$_2$—C$_6$H$_4$ |
| H | 2-F, 4-OCHF$_2$—C$_6$H$_3$ |
| H | 3-CO$_2$CH$_3$—C$_6$H$_4$ |
| H | 4-CO$_2$CH$_3$—C$_6$H$_4$ |
| H | 4-CO$_2$C(CH$_3$)$_3$—C$_6$H$_4$ |
| H | 2,3-[OCH$_2$O]—C$_6$H$_3$ |
| H | 3,4-[OCH$_2$O]—C$_6$H$_3$ |
| H | 3,4-[OC(CH$_3$)$_2$O]—C$_6$H$_3$ |
| H | 3,4-[OCH$_2$CH$_2$O]—C$_6$H$_3$ |
| H | 2,3-[(CH$_2$)$_4$]—C$_6$H$_3$ |
| H | 3,4-[(CH$_2$)$_4$]—C$_6$H$_3$ |
| H | 2,3-[CH=CH—CH=CH]—C$_6$H$_3$ |
| H | 3,4-[CH=CH—CH=CH]—C$_6$H$_3$ |
| H | CH$_3$ |
| H | CH$_2$CH$_3$ |
| H | (CH$_2$)$_2$CH$_3$ |
| H | CH(CH$_3$)$_2$ |
| H | (CH$_2$)$_3$CH$_3$ |
| H | CH$_2$CH(CH$_3$)$_2$ |
| H | CH(CH$_3$)CH$_2$CH$_3$ |
| H | C(CH$_3$)$_3$ |
| H | Cyclopropyl |
| H | Cyclopentyl |
| H | Cyclohexyl |
| H | 2-Tetrahydropyranyl |
| H | 3-Tetrahydropyranyl |
| H | 2-Tetrahydrofuranyl |
| H | 2-Tetrahydrofuranyl |
| H | 2-Pyridyl |
| H | 4-Cl-Pyridin-2-yl |
| H | 5-Cl-Pyridin-2-yl |
| H | 6-Cl-Pyridin-2-yl |
| H | 5-CF$_3$-Pyridin-2-yl |
| H | 3,5-(CF$_3$)$_2$-Pyridin-2-yl |
| H | 5-Cl, 3-CF$_3$-Pyridin-2-yl |
| H | 3-Cl, 5-CF$_3$-Pyridin-2-yl |
| H | 4-CF$_3$, 6-CH$_3$-Pyridin-2-yl |
| H | 3-Pyridyl |
| H | 6-CH$_3$-Pyridin-3-yl |
| H | 4-Pyridyl |
| H | 2,6-(CH$_3$)$_2$-Pyridin-4-yl |
| H | 6-Cl-Pyridazin-3-yl |
| H | 4-CF$_3$-Pyrimidin-2-yl |
| H | 5-Cl-Pyrimidin-2-yl |
| H | 6-CF$_3$-Pyrimidin-4-yl |
| H | 5-Cl-Pyrazin-2-yl |
| H | 4-CH$_3$-Thiazol-2-yl |
| H | 5-CH$_3$-Thiazol-2-yl |
| H | 5-Cyclopropyl-isoxazol-3-yl |
| H | 3-C$_6$H$_5$-Isoxazol-5-yl |

The compounds of the formula I are suitable for effectively controlling pests of the insects, arachnids and nematodes class. They can be employed as fungicides and pesticides in the crop protection and in the hygiene, stored material protection and veterinary sector.

The harmful insects include from the order of the butterflies (Lepidoptera), for example, *Agrotis ypsilon, Agrotis segetum, Alabama argillacea, Anticarsia gemmatalis, Argyresthia conjugella, Autographa gamma, Bupalus piniarius, Cacoecia murinana, Capua reticulana, Cheimatobia brumata, Choristoneura fumiferana, Choristoneura occidentalis, Cirphis unipuncta, Cydia pomonella, Dendrolimus pini, Diaphania nitidalis, Diatraea grandiosella, Earias insulana, Elasmopalpus lignosellus, Eupoecilia ambiguella, Evetria bouliana, Feltia subterranea, Galleria mellonella, Grapholitha funebrana, Grapholitha molesta, Heliothis armigera, Heliothis virescens, Heliothis zea, Hellula undalis, Hibernia defoliaria, Hyphantria cunea, Hyponomeuta malinellus, Keiferia lycopersicella, Lambdina fiscellaria,*

Laphygma exigua, Leucoptera coffeella, Leucoptera scitella, Lithocolletis blancardella, Lobesia botrana, Loxostege sticticalis, Lymantria dispar, Lymantria monacha, Lyonetia clerkella, Malacosoma neustria, Mamestra brassicae, Orgyia pseudotsugata, Ostrinia nubilalis, Panolis flammea, Pectinophora gossypiella, Peridroma saucia,, Phalera bucephala, Phthorimaea operculella, Phyllocnistis citrella, Pieris brassicae, Plathypena scabra, Plutella xylostella, Pseudoplusia includens, Rhyacionia frustrana, Scrobipalpula absoluta, Sitotroga cerealella, Sparganothis pilleriana, Spodoptera frugiperda, Spodoptera littoralis, Spodoptera litura, Thaumatopoea pityocampa, Tortrix viridana, Trichoplusia ni, Zeiraphera canadensis.

From the order of the beetles (Coleoptera), for example, Agrilus sinuatus, Agriotes lineatus, Agriotes obscurus, Amphimallus solstitialis, Anisandrus dispar, Anthonomus grandis, Anthonomus pomorum, Atomaria linearis, Blastophagus piniperda, Blitophaga undata, Bruchus rufimanus, Bruchus pisorum, Bruchus lentis, Byctiscus betulae, Cassida nebulosa, Cerotoma trifurcata, Ceuthorrhynchus assimilis, Ceuthorrhynchus napi, Chaetocnema tibialis, Conoderus vespertinus, Crioceris asparagi, Diabrotica longicornis, Diabrotica 12-punctata, Diabrotica virgifera, Epilachna varivestis, Epitrix hirtipennis, Eutinobothrus brasiliensis, Hylobius abietis, Hypera brunneipennis, Hypera postica, Ips typographus, Lema bilineata, Lema melanopus, Leptinotarsa decemlineata, Limonius californicus, Lissorhoptrus oryzophilus, Melanotus communis, Meligethes aeneus, Melolontha hippocastani, Melolontha melolontha, Oulema oryzae, Otiorrhynchus sulcatus, Otiorrhynchus ovatus, Phaedon cochleariae, Phyllotreta chrysocephala, Phyllophaga sp., Phyllopertha horticola, Phyllotreta nemorum, Phyllotreta striolata, Popillia japonica, Sitona lineatus, Sitophilus granaria.

From the order of the dipterous insects (Diptera), for example, Aedes aegypti, Aedes vexans, Anastrepha ludens, Anopheles maculipennis, Ceratitis capitata, Chrysomya bezziana, Chrysomya hominivorax, Chrysomya macellaria, Contarinia sorghicola, Cordylobia anthropophaga, Culex pipiens, Dacus cucurbitae, Dacus oleae, Dasineura brassicae, Fannia canicularis, Gasterophilus intestinalis, Glossina morsitans, Haematobia irritans, Haplodiplosis equestris, Hylemyia platura, Hypoderma lineata, Liriomyza sativae, Liriomyza trifolii, Lucilia cuprina, Lucilia sericata, Lycoria pectoralis, Mayetiola destructor, Musca domestica, Muscina stabulans, Oestrus ovis, Oscinella frit, Pegomya hysocyami, Phorbia antiqua, Phorbia brassicae, Phorbia coarctata, Rhagoletis cerasi, Rhagoletis pomonella, Tabanus bovinus, Tipula oleracea, Tipula paludosa.

From the order of the thrips (Thysanoptera), for example, Frankliniella fusca, Frankliniella occidentalis, Frankliniella tritici, Scirtothrips citri, Thrips oryzae, Thrips palmi, Thrips tabaci.

From the order of the hymenopterous insects (Hymenoptera), for example, Athalia rosae, Atta cephalotes, Atta sexdens, Atta texana, Hoplocampa minuta, Hoplocampa testudinea, Monomorium pharaonis, Solenopsis geminata, Solenopsis invicta.

From the order of the bed bugs (Heteroptera), for example, Acrosternum hilare, Blissus leucopterus, Cyrtopeltis notatus, Dysdercus cingulatus, Dysdercus intermedius, Eurygaster integriceps, Euchistus impictiventris, Leptoglossus phyllopus, Lygus lineolaris, Lygus pratensis, Nezara viridula, Piesma quadrata, Solubea insularis, Thyanta perditor.

From the order of the plant-sucking insects (Homoptera), for example, Acyrthosiphon onobrychis, Adelges laricis, Aphidula nasturtii, Aphis fabae, Aphis pomi, Aphis sambuci, Brachycaudus cardui, Brevicoryne brassicae, Cerosipha gossypii, Dreyfusia nordmannianae, Dreyfusia piceae, Dysaphis radicola, Dysaulacorthum pseudosolani, Empoasca fabae, Macrosiphum avenae, Macrosiphum euphorbiae, Macrosiphon rosae, Megoura viciae, Metopolophium dirhodum, Myzodes persicae, Myzus cerasi, Nilaparvata lugens, Pemphigus bursarius, Perkinsiella saccharicida, Phorodon humuli, Psylla mali, Psylla piri, Rhopalomyzus ascalonicus, Rhopalosiphummaidis, Sappaphis mala, Sappaphis mali, Schizaphis graminum, Schizoneura lanuginosa, Trialeurodes vaporariorum, Viteus vitifolii.

From the order of the termites (Isoptera), for example, Calotermes flavicollis, Leucotermes flavipes, Reticulitermes lucifugus, Termes natalensis.

From the order of the orthopterous insects (Orthoptera), for example, Acheta domestica, Blatta orientalis, Blattella germanica, Forficula auricularia, Gryllotalpa gryllotalpa, Locusta migratoria, Melanoplus bivittatus, Melanoplus femur-rubrum, Melanoplus mexicanus, Melanoplus sanguinipes, Melanoplus spretus, Nomadacris septemfasciata, Periplaneta americana, Schistocerca americana, Schistocerca peregrina, Stauronotus maroccanus, Tachycines asynamorus.

From the class of the Arachnoidea, for example, arachnids (Acarina) such as Amblyomma americanum, Amblyomma variegatum, Argas persicus, Boophilus annulatus, Boophilus decoloratus, Boophilus microplus, Brevipalpus phoenicis, Bryobia praetiosa, Dermacentor silvarum, Eotetranychus carpini, Eriophyes sheldoni, Hyalomma truncatum, Ixodes ricinus, Ixodes rubicandus, Ornithodorus moubata, Otobius megnini, Paratetranychus pilosus, Dermanyssinus gallinae, Phyllocoptruta oleivora, Polyphagotarsonemus latus, Psoroptes ovis, Rhipicephalus appendiculatus, Rhipicephalus evertsi, Sarcoptes scabiei, Tetranychus cinnabarinus, Tetranychus kanzawai, Tetranychus pacificus, Tetranychus telarius, Tetranychus urticae.

From the class of the nematodes, for example, root gall nematodes, e.g. Meloidogyne hapla, Meloidogyne incognita, Meloidogyne javanica, cyst-forming nematodes, e.g. Globodera rostochiensis, Heterodera avenae, Heterodera glycines, Heterodera schachtii, Heterodera trifolii, stem and leaf eelworms, e.g. Belonolaimus longicaudatus, Ditylenchus destructor, Ditylenchus dipsaci, Heliocotylenchus multicinctus, Longidorus elongatus, Radopholus similis, Rotylenchus robustus, Trichodorus primitivus, Tylenchorhynchus claytoni, Tylenchorhynchus dubius, Pratylenchus neglectus, Pratylenchus penetrans, Pratylenchus curvitatus, Pratylenchus goodeyi.

The active compounds can be used as such, in the form of their formulations or the use forms prepared therefrom by spraying, atomizing, dusting, broadcasting or watering, e.g. in the form of directly sprayable solutions, powders, suspensions or dispersions, emulsions, oil dispersions, pastes, dusting compositions, broadcasting compositions or granules. The use forms depend entirely on the intended uses; in each case they should if possible guarantee the finest dispersion of the active compounds according to the invention.

The active compound concentrations in the ready-to-use preparation can be varied within relatively wide ranges.

In general, they are from 0.0001 to 10%, preferably from 0.01 to 1%.

The active compounds can also be used with great success in the ultra-low volume process (ULV), it being possible to apply formulations containing more than 95% by weight of active compound or even the active compound without additives.

The application rate of active compound for controlling pests under outdoor conditions is from 0.1 to 2.0, preferably from 0.2 to 1.0 kg/ha.

To prepare directly sprayable solutions, emulsions, pastes or oil dispersions, mineral oil fractions of medium to high boiling point, such as kerosene or diesel oil, additionally coal tar oils and oils of vegetable or animal origin, aliphatic, cyclic and aromatic hydrocarbons, e.g. benzene, toluene, xylene, paraffin, tetrahydronaphthalene, alkylated naphthalenes or their derivatives, methanol, ethanol, propanol, butanol, chloroform, carbon tetrachloride, cyclohexanol, cyclohexanone, chlorobenzene, isophorone, strongly polar solvents, e.g. dimethylformamide, dimethyl sulfoxide, N-methylpyrrolidone and water are suitable.

Aqueous use forms can be prepared from emulsion concentrates, pastes or wettable powders (oil dispersions) by addition of water. To prepare emulsions, pastes or oil dispersions, the substances can be homogenized in water as such or dissolved in an oil or solvent, by means of wetting agents, adhesives, dispersants or emulsifiers. However, concentrates consisting of active substance, wetting agent, adhesive, dispersant or emulsifier and possibly solvent or oil can also be prepared which are suitable for dilution with water.

Suitable surface-active substances are alkali metal, alkaline earth metal and ammonium salts of lignosulfonic acid, naphthalenesulfonic acid, phenolsulfonic acid, dibutylnaphthalenesulfonic acid, alkylarylsulfonates, alkylsulfates, alkylsulfonates, fatty alcohol sulfates and fatty acids and their alkali metal and alkaline earth metal salts, salts of sulfated fatty alcohol glycol ethers, condensation products of sulfonated naphthalene and naphthalene derivatives with formaldehyde, condensation products of naphthalene or of naphthalenesulfonic acid with phenol and formaldehyde, polyoxyethylene octyl phenol ethers, ethoxylated isooctylphenol, octylphenol, nonylphenol, alkylphenol polyglycol ethers, tributylphenyl polyglycol ethers, alkylaryl polyether alcohols, isotridecyl alcohol, fatty alcohol-ethylene oxide condensates, ethoxylated castor oil, polyoxyethylene alkyl ethers, ethoxylated polyoxypropylene, lauryl alcohol polyglycol ether acetal, sorbitol esters, lignin-sulfite waste liquors and methylcellulose.

Powder, scattering and dusting compositions can be prepared by mixing or joint grinding of the active substances with a solid carrier.

The formulations in general contain from 0.01 to 95% by weight, preferably from 0.1 to 90% by weight, of the active compound. The active compounds are employed here in a purity of from 90% to 100%, preferably from 95% to 100% (according to NMR spectrum). Examples of formulations are:

I. 5 parts by weight of a compound according to the invention are intimately mixed with 95 parts by weight of finely divided kaolin. A dusting composition is obtained in this way which contains 5% by weight of the active compound.

II. 30 parts by weight of a compound according to the invention are intimately mixed with a mixture of 92 parts by weight of powdered silica gel and 8 parts by weight of liquid paraffin which has been sprayed onto the surface of this silica gel. In this way a preparation of the active compound having good adhesion is obtained (active compound content 23% by weight).

III. 10 parts by weight of a compound according to the invention are dissolved in a mixture which consists of 90 parts by weight of xylene, 6 parts by weight of the addition product of from 8 to 10 mol of ethylene oxide to 1 mol of oleic acid N-monoethanolamide, 2 parts by weight of calcium salt of dodecylbenzenesulfonic acid and 2 parts by weight of the addition product of 40 mol of ethylene oxide to 1 mol of castor oil (active compound content 9% by weight).

IV. 20 parts by weight of a compound according to the invention are dissolved in a mixture which consists of 60 parts by weight of cyclohexanone, 30 parts by weight of isobutanol, 5 parts by weight of the addition product of 7 mol of ethylene oxide to 1 mol of isooctylphenol and 5 parts by weight of the addition product of 40 mol of ethylene oxide to 1 mol of castor oil (active compound content 16% by weight).

V. 80 parts by weight of a compound according to the invention are well mixed with 3 parts by weight of the sodium salt of diisobutylnaphthalene-alpha-sulfonic acid, 10 parts by weight of the sodium salt of a lignosulfonic acid from a sulfite waste liquor and 7 parts by weight of powdered silica gel and the mixture is ground in a hammer mill (active compound content 80% by weight).

VI. 90 parts by weight of a compound according to the invention are mixed with 10 parts by weight of N-methyl-α-pyrrolidone and a solution is obtained which is suitable for use in the form of very small drops (active compound content 90% by weight).

VII. 20 parts by weight of a compound according to the invention are dissolved in a mixture which consists of 40 parts by weight of cyclohexanone, 30 parts by weight of isobutanol, 20 parts by weight of the addition product of 7 mol of ethylene oxide to 1 mol of isooctylphenol and 10 parts by weight of the addition product of 40 mol of ethylene oxide to 1 mol of castor oil. By pouring the solution into and finely dispersing it in 100,000 parts by weight of water, an aqueous dispersion is obtained which contains 0.02% by weight of the active compound.

VIII. 20 parts by weight of a compound according to the invention are well mixed with 3 parts by weight of the sodium salt of diisobutylnaphthalene-α-sulfonic acid, 17 parts by weight of the sodium salt of a lignosulfonic acid from a sulfite waste liquor and 60 parts by weight of powdered silica gel and the mixture is ground in a hammer mill. By finely dispersing the mixture in 20,000 parts by weight of water, a spray mixture is obtained which contains 0.1% by weight of the active compound.

Granules, e.g. coated, impregnated and homogeneous granules, can be prepared by binding the active compounds to solid carriers. Solid carriers are e.g. mineral earths, such as silica gel, silicic acids, silicates, talc, kaolin, attaclay, limestone, lime, chalk, bole, loess, clay, dolomite, diatomaceous earth, calcium sulfate and magnesium sulfate, magnesium oxide, ground synthetic materials, fertilizers, such as e.g. ammonium sulfate, ammonium phosphate, ammonium nitrate, ureas, and vegetable products, such as cereal flour, tree bark, wood and nutshell meal, cellulose powder and other solid carriers.

Oils of various types, herbicides, fungicides, other pesticides and bactericides can be added to the active compounds, if appropriate even immediately before use (tank mix). These agents can be admixed to the agents according to the invention in a weight ratio of from 1:10 to 10:1.

SYNTHESIS EXAMPLES

The procedures given in the Synthesis Examples below were utilized with appropriate modification of the starting compounds to obtain further compounds I. The compounds thus obtained are listed in the following Tables with physical data.

EXAMPLE 1

N-Methyl-E-2-methoxyimino-2-[(2-methylphenoxymethyl)phenyl]acetamide 250 g of methyl E-2-methoxyimino-2-[(2-methylphenoxymethyl)phenyl]acetate are suspended in 1 l of 40% strength aqueous methylamine solution and heated at 40° C. for 4 h. After cooling to room temperature (20° C.), the solid is filtered off with suction, washed several times with water and dried at 50° C. 229.8 g of the title compound are obtained as colorless crystals.

M.p.: 109°–112° C.

$^1$H-NMR (CDCl$_3$, δ in ppm): 2.20 (s, 3H); 2.85 (d, 3H); 3.95 (s, 3H); 4.90 (s, 2H); 6.7 (NH); 6.8–7.6 (m, 8H)

EXAMPLE 2

N-Methyl-E-2-Methoxyimino-2-[(2-chloromethyl)-phenyl]acetamide 2 g of methyl E-2-methoxyimino-2-[(2-methylphenoxymethyl)phenyl]acetate from Example 1 are initially introduced in 30 ml of anhydrous dichloromethane at 10° C. 9.4 g of boron trichloride solution (1-molar solution in n-hexane) are added dropwise, the mixture is refluxed for 1.5 h and cooled to 10° C., a further 9.4 g of boron trichloride solution are added and the mixture is stirred overnight at room temperature (20° C.). After adding 8.2 g of methanol dropwise, the mixture is concentrated in a rotary evaporator. The residue is taken up in 100 ml of dichloromethane and the solution is washed with 5% sodium hydroxide solution and then with water. The organic phase is finally dried over sodium sulfate. After stripping off the solvent 1.2 g of the title compound remain as an oil.

$^1$H-NMR (CDCl$_3$, δ in ppm): 2.95 (d, 3H); 3.90 (s, 3H); 4.45 (s, 2H); 6.8 (NH); 7.1–7.6 (m, 4H)

EXAMPLE 3

N-Methyl-E-2-methoxyimino-2-[(2-bromomethyl)-phenyl]acetamide 10 g of N-methyl-E-2-methoxyimino-2-[(2-methylphenoxymethyl)phenyl]acetamide from Example 1 are initially introduced in 50 ml of anhydrous dichloromethane. Hydrogen bromide is passed into the solution until the saturation concentration is reached (about 9 g of HBr). After stirring at room temperature for 68 h, the starting material has completely reacted. After adding a further 50 ml of dichloromethane, the mixture is worked up as in Example 2. 7.0 g of the title compound remain as an oil which crystallizes completely on allowing to stand.

M.p.: 128°–129° C.

$^1$H-NMR (CDCl$_3$, δ in ppm): 2.95 (d, 3H); 3.95 (s, 3H); 4.35 (s, 2H); 6.85 (NH); 7.1–7.5 (m, 4H)

EXAMPLE 4

N-methyl-E-2-methoxyimino-2-[(2-dimethylphosphonomethyl)phenyl]acetamide 15 g of N-methyl-E-2-methoxyimino-2-[(2-bromomethyl)phenyl]acetamide are heated at 110° C. for 3 h in 50 ml of trimethyl phosphite. After conversion of the bromide is complete, excess trimethyl phosphite is distilled off at about 15 mm Hg. The residue is taken up in 200 ml of dichloromethane, washed several times with saturated NaCl solution and dried over sodium sulfate. After stripping off the solvent 12.8 g of a viscous, brown oil remain.

$^1$H-NMR (CDCl$_3$, δ in ppm): 2.9 (d, 3H); 3.0 (s, 1H); 3.15 (s, 1H); 3.55 (s, 3H); 3.65 (s, 3H); 3.95 (s, 3H); 7.0–7.5 (m, 5H)

EXAMPLE 5

N-methyl-E-2-methoxyimino-2-[2-(E-2-[1-(4-chlorophenyl)pyrazol-4-yl]ethenyl)phenyl]acetamide 3.1 g of 1-(4-chlorophenyl)-4-formylpyrazole and 5.65 g of the phosphonate from Example 4 are dissolved in 30 ml of anhydrous dimethylformamide. 0.43 g of sodium hydride are added to this solution at room temperature. The mixture foams, the temperature increasing from 21° C. to 38° C. After stirring for a further 2 hours, the mixture is poured into ice-water. The precipitate which is deposited during the course of this is filtered off with suction and taken up in ethyl acetate. The organic phase is washed several times with saturated sodium chloride solution, dried over Na$_2$SO$_4$ and concentrated in a rotary evaporator. The residual solid is stirred with 40 ml of ethyl acetate and filtered off with suction. 3.0 g of the title compound are obtained as a colorless solid.

M.p.: 188°–190° C.

$^1$H-NMR (CDCl$_3$, δ in ppm): 2.95 (d, 3H); 4.0 (s, 3H); 6.7 (d, 1H); 6.8 (br, NH); 6.9 (d, 1H); 7.15 (d, 1H); 7.25–7.7 (m, 7H); 7.8 (s, 1H); 7.9 (s, 1H)

EXAMPLE 6

N-methyl-E-2-methoxyimino-2-[2-(E-2-[1-(2,4-dichlorophenyl)-5-methylpyrazol-4-yl]ethenyl)-phenyl]acetamide 3.8 g of 1-(2,4-dichlorophenyl)-4-formyl-5-methylpyrazole and 4.7 g of the phosphonate from Example 4 are reacted in 80 ml of anhydrous dimethylformamide in a similar manner to Example 5. 3.4 g of crude product are obtained, 2.2 g of the title compound remaining as a colorless solid after titrating with diisopropyl ether.

M.p.: 165°–168° C.

$^1$H-NMR (CDCl$_3$, δ in ppm): 2.2 (s, 3H); 2.95 (d, 3H); 4.0 (s, 3H); 6.7 (d, $^1$H); 6.8 (br, NH); 6.9 (d, 1H); 7.2 (d, 1H); 7.3–7.5 (m, 4H); 7.6 (s, 1H); 7.7 (d, 1H); 7.85 (s, 1H)

EXAMPLE 7

N-Methyl-E-2-methoxyimino-2-[2-(E-2-[1-(2,4-dichlorophenyl)pyrazol-3-yl]ethenyl)phenyl]acetamide 3.6 g of 1-(2,4-dichlorophenyl)-3-formylpyrazole and 4.7 g of the phosphonate from Example 4 are reacted in 80 ml of anhydrous dimethylformamide in a similar manner to Example 5. 4.2 g of crude product are obtained, from which the E isomer can be isolated by column chromatography (silica gel, eluent toluene/ethyl acetate 9:1 to 8:2, v/v).

E isomer: 2.0 g of colorless solid

M.p.: 151°–152° C.

$^1$H-NMR (CDCl$_3$, δ in ppm): 2.9 (d, 3H); 3.95 (s, 3H); 6.6 (d, 1H); 6.7 (br, NH); 6.9 (d, 1H); 7.0–7.6 (m, 8H); 7.75 (d, 1H); 7.9 (d, 1H) N-Ethyl-E-2-methoxyimino-2-[2-(E-2-[1-(2,4-dichlorophenyl)-5-trifluoromethylpyrazol-4-yl]acetamide are initially introduced in 30 ml of anhydrous toluene. After addition of 1.2 g of Lawesson reagent (2,4-bis(4-methoxyphenyl)-1,3-dithia-2,4-diphosphetane-2,4-disulfide), the mixture is refluxed for 8 hours, the suspension clearing. After cooling, the solvent is stripped off on a rotary evaporator. After purification by column chromatography (silica gel, eluent toluene→toluene/ethyl acetate 8:2), 1.2 g of the useful product were obtained as a brown oil from the residue which remained.

$^1$H-NMR (CDCl$_3$, δ in ppm): 3.3 (2.34H; 3.95 (s, 3H); 6.80 (d, 1H); 6.95 (s, 1H); 7.10 (d, 14); 7.2–7.5 (m,); 17.6 (s, 1H); 6.7 (d, 1H), 7.9 (s, 1H), 8.8 (NH)

IR [cm$^{-1}$] 3280, 2940, 1520, 1497, 1173, 1132, 1027

TABLE Ia

| No. | $R^1_n$ | $R^2$ | $R^3_m$ | $R^4$ | * | # | M.p. (°C.) |
|---|---|---|---|---|---|---|---|
| Ia.001 | H | 2,4-Cl$_2$—C$_6$H$_4$ | 5-CF$_3$ | H | E | E | 161–163 |
| Ia.002 | H | 3-Cl—C$_6$H$_4$ | 5-CF$_3$ | H | E | E | 153–154 |
| Ia.003 | H | 4-CH$_3$—C$_6$H$_4$ | 5-CF$_3$ | H | E | E | 139–142 |
| Ia.004 | H | 4-Cl—C$_6$H$_4$ | 5-CF$_3$ | H | E | E | 152–155 |
| Ia.005 | H | 2,4-Cl$_2$—C$_6$H$_3$ | H | H | E | E | 120–123 |
| Ia.006 | H | 4-Cl—C$_6$H$_4$ | H | H | E | E | 188–190 |
| Ia.007 | H | CH$_3$ | 3-CH$_3$, 5-Cl | H | E | E | 140–142 |
| Ia.008 | H | 2,4-Cl$_2$—C$_6$H$_3$ | 5-CH$_3$ | H | E | E | 165–168 |
| Ia.009 | H | 2,4-Cl$_2$—C$_6$H$_3$ | 5-Cl | H | E | E | 195–162 |
| Ia.010 | H | 4-Cl—C$_6$H$_4$ | 5-Cl | H | E | E | 165–167 |
| Ia.011 | H | 3-Cl—C$_6$H$_4$ | 5-Cl | H | E | E | 143–144 |
| Ia.012 | H | C$_6$H$_5$ | H | H | E | E | 202–204 |
| Ia.013 | H | 2-Cl—C$_6$H$_4$ | 5-CF$_3$ | H | E | E | 126–128 |
| Ia.014 | H | 4-F—C$_6$H$_4$ | 5-CF$_3$ | H | E | E | 121–123 |
| Ia.015 | H | 3,5-Cl$_2$—C$_6$H$_3$ | 5-CF$_3$ | H | E | E | 188–190 |
| Ia.016 | H | 4-OCH$_3$—C$_6$H$_4$ | 5-CF$_3$ | H | E | E | 130–132 |
| Ia.017 | H | 3-CH$_3$—C$_6$H$_4$ | 5-CF$_3$ | H | E | E | 150–152 |

* Configuration of the double bond in relation to the pyrazole and the phenyl radical
Configuration of the double bond in relation to the OCH$_3$ and CONHCH$_3$ group TABLE Ib

| No. | $R^1_n$ | $R^2$ | $R^3_m$ | $R^4$ | * | # | M.p. (°C.) |
|---|---|---|---|---|---|---|---|
| Ib.001 | H | 2,4-Cl$_2$—C$_6$H$_4$ | H | H | E | E | 151–152 |
| Ib.002 | H | 4-Cl—C$_6$H$_4$ | H | H | E | E | 173–176 |
| Ib.003 | H | 3-Cl—C$_6$H$_4$ | H | H | E | E | 137–140 |

* Configuration of the double bond in relation to the pyrazole and the phenyl radical
Configuration of the double bond in relation to the OCH$_3$ and CONHCH$_3$ group

USE EXAMPLES

It was possible to show the insecticidal action of the compounds of the general formula I by the following tests:

The active compounds were prepared a) as a 0.1% strength solution in acetone or b) as a 10% strength emulsion in a mixture of 70% by weight of cyclohexanone, 20% by weight of Nekanil® LN (Lutensol® AP6, wetting agent having emulsifier and dispersant action based on ethoxylated alkylphenols) and 10% by weight of Emulphor® EL (Emulan® EL, emulsifier based on ethoxylated fatty alcohols) and diluted with acetone in the case of a) or with water in the case of b) according to the desired concentration.

After conclusion of the tests, the lowest concentration was in each case determined at which the compounds still caused an 80–100% inhibition or mortality in comparison with untreated control tests (activity threshold or minimum concentration).

Action against Pyricularia oryzae (rice blast)

Rice seedlings (variety: Tai Nong 67) were sprayed with the active compound preparation (application rate: 250 ppm) until dripping wet. After 24 hours, the plants were sprayed with an aqueous spore suspension of the fungus *Pyricularia oryzae* and stored for 6 days at 22°–24° C. at a relative atmospheric humidity of 95–99%. Assessment was carried out visually.

In this test, the plants treated with the compounds Ia.008, Ia.009, Ia.011, Ia.012, Ia.013 and Ia.014 showed an attack of 15% and less while the untreated plants were attacked to 70%.

Action against Plasmopara viticola (vine Peronospora).

Potted vines (variety: Müller Thurgau) were sprayed with the active compound preparation (application rate: 63 ppm) until dripping wet. After 8 days, the plants were sprayed with a zoospore suspension of the fungus *Plasmopara viticola* and stored for 5 days at 20°–30° C. at high atmospheric humidity. Before assessment, the plants were then stored for 16 h at high atmospheric humidity. Assessment was carried out visually.

In this test, the plants treated with the compounds Ia.009, Ia.010, Ia.011, Ia.012, Ia.013, Ia.014, Ia.016 and Ia.017 showed an attack of 5% or less while the untreated plants were attacked to 80%.

We claim:

1. A pyrazolyl derivative of the general formula I

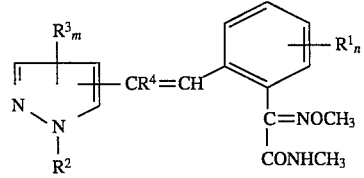

where the indices and the substituents have the following meanings:

n is 0, 1, 2, 3 or 4, it being possible for the radicals R$^1$ to be different if n is greater than 1;

m is 0, 1 or 2, it being possible for the radicals R$^3$ to be different if m is greater than 1;

R$^1$ is nitro, cyano, halogen,
  C$_1$–C$_4$-alkyl, C$_1$–C$_4$-haloalkyl, C$_1$–C$_4$-alkoxy, C$_1$–C$_4$-haloalkoxy, C$_1$–C$_4$-alkylthio,
  phenyl or phenoxy, where the aromatic radicals can carry one to five halogen atoms and/or one to three of the following radicals: nitro, cyano, C$_1$–C$_4$-alkyl, C$_1$–C$_4$-haloalkyl, C$_1$–C$_4$-alkoxy, C$_1$–C$_4$-haloalkoxy and C$_1$–C$_4$-alkylthio;
  or in the case where n is greater than 1, a 1,3-butadiene-1,4-diyl group bonded to two adjacent C atoms of the phenyl radical, which in turn can carry one to four halogen atoms and/or one or two of the following radicals: nitro, cyano, $C_1$–$C_4$-alkyl, $C_1$–$C_4$-haloalkyl, $C_1$–$C_4$-alkoxy, $C_1$–$C_4$-haloalkoxy and $C_1$–$C_4$-alkylthio;

$R^2$ is hydrogen,
unsubstituted or substituted alkyl, alkenyl or alkynyl,
an unsubstituted or substituted, saturated or mono- or diunsaturated ring which, in addition to carbon atoms, can carry one to three of the following heteroatoms: oxygen, sulfur and nitrogen, or
an unsubstituted or substituted, mono- or binuclear aromatic radical which, in addition to carbon atoms, can contain one to four nitrogen atoms and one oxygen or sulfur atom or one oxygen or sulfur atom as ring members;

$R^3$ is nitro, cyano, halogen, $C_1$–$C_4$-alkyl, $C_1$–$C_4$-haloalkyl, $C_1$–$C_4$-alkoxy or $C_1$–$C_4$-haloalkoxy;

$R^4$ is hydrogen, cyano, halogen, $C_1$–$C_4$-alkyl or $C_1$–$C_4$-haloalkyl.

2. A composition suitable for controlling pests, containing a solid or liquid carrier and a compound of the general formula I as claimed in claim 1.

3. A method of controlling pests, which comprises treating the pests or the materials, plants, soil or seed to be protected from them with an active amount of a compound of the general formula I as claimed in claim 1.

4. A compound as defined in claim 1 of the formula

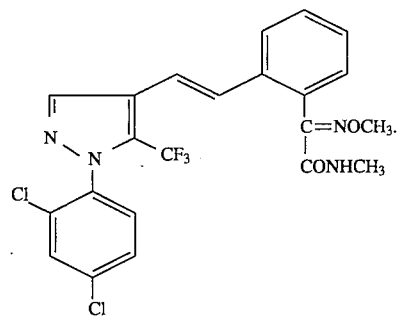

* * * * *

UNITED STATES PATENT AND TRADEMARK OFFICE
CERTIFICATE OF CORRECTION

PATENT NO.: 5,506,254
DATED: April 9, 1996
INVENTOR(S): KIRSTGEN et al.

It is certified that error appears in the above-identified patent and that said Letters Patent is
hereby corrected as shown below:

On the cover page, item [54], "PYRAZOYLY" should be --PYRAZOLYL--.

On the cover page, insert the following information:

--Attorney, Agent or Firm: Keil & Weinkauf--; and

--[73] Assignee: BASF Aktiengesellschaft, Ludwigshafen, Germany--.

Signed and Sealed this

Twenty-fourth Day of September, 1996

Attest:

BRUCE LEHMAN

Attesting Officer         Commissioner of Patents and Trademarks